United States Patent [19]

Kleiman

[11] Patent Number: 5,295,995
[45] Date of Patent: Mar. 22, 1994

[54] PERFUSION DILATATION CATHETER

[76] Inventor: Jay H. Kleiman, 2412 Lawndale, Evanston, Ill. 60201

[21] Appl. No.: 937,051

[22] Filed: Aug. 27, 1992

[51] Int. Cl.$^5$ ............................................. A61M 29/02
[52] U.S. Cl. ...................................... 606/194; 604/96
[58] Field of Search ............... 604/96, 101; 606/194, 606/192

[56] References Cited

U.S. PATENT DOCUMENTS

| | | |
|---|---|---|
| 2,930,377 | 3/1960 | Cowley . |
| 3,889,686 | 6/1975 | Duturbure . |
| 4,040,413 | 8/1977 | Ohshiro . |
| 4,183,102 | 1/1980 | Guiset ............................ 604/101 X |
| 4,233,983 | 11/1980 | Rocco . |
| 4,329,993 | 5/1982 | Lieber et al. . |
| 4,423,725 | 1/1984 | Baran et al. . |
| 4,581,017 | 4/1986 | Sahota ............................ 604/101 |
| 4,601,713 | 7/1986 | Fuqua . |
| 4,661,094 | 4/1987 | Simpson . |
| 4,710,181 | 12/1987 | Fuqua . |
| 4,738,666 | 4/1988 | Fuqua . |
| 4,787,388 | 11/1988 | Hofmann ............................ 606/194 |
| 4,790,315 | 12/1988 | Mueller, Jr. et al. . |
| 4,795,427 | 1/1989 | Helzel ............................ 604/53 |
| 4,877,031 | 10/1989 | Conway et al. . |
| 4,878,495 | 11/1989 | Grayzel ............................ 604/101 X |
| 4,892,519 | 1/1990 | Songer et al. . |
| 4,909,252 | 3/1990 | Goldberger . |
| 5,102,416 | 4/1992 | Rock ............................ 606/194 |
| 5,167,628 | 12/1992 | Boyles ............................ 604/101 |

FOREIGN PATENT DOCUMENTS 400713 12/1990 European Pat. Off. .

OTHER PUBLICATIONS

"Interventional Catheterization Techniques," pp. 1379-1387, published 1988, W. B. Saunders Co., Philadelphia, Pa.

Primary Examiner—C. Fred Rosenbaum
Assistant Examiner—Corrine Maglione
Attorney, Agent, or Firm—Wallenstein, Wagner & Hattis, Ltd.

[57] ABSTRACT

The present invention relates to angioplasty dilatation catheters. Specifically, the perfusion dilatation catheter of the present invention is used in coronary angioplasty, but it is equally applicable to renal, cerebral, and peripheral angioplasties. The catheter is comprised of a long flexible tubular shaft having an expandable balloon affixed near the distal end of the shaft and surrounding the circumference of the shaft. Upon expansion, the balloon's cross-section is circumscribed by the circular perimeter of the target vessel cross-section. The balloon tip has a minimum of two rounded apices, wherein the maximum height of the apices does not exceed the nominal radius of the target vessel, and further wherein multiple radii of the balloon tip cross-section are of lesser radial dimension than the nominal radius of the target vessel. Thus, due to the unique shape and configuration of the balloon, a path for blood to flow past the balloon tip during expansion is formed through the areas of submaximal tip radial dimension. The remainder of the dilatation catheter incorporates conventional catheter features, including at least one lumen.

20 Claims, 2 Drawing Sheets

PERFUSION DILATATION CATHETER

TECHNICAL FIELD

This invention pertains generally to medical devices, and specifically to dilatation catheters for use in coronary, renal, cerebral, and peripheral angioplasty. Specifically, the invention is directed to a dilatation catheter comprised of a flexible elongated tubular shaft having proximal and distal ends, at least one lumen, and an inflatable balloon affixed near the distal end of the shaft and surrounding the circumference of the tubular shaft. Upon expansion, the balloon becomes non-circular, and the balloon's cross-section is circumscribed by the circular perimeter of the target vessel cross-section. The balloon tip has at least two substantially rounded axial protrusions or apices which, upon expansion of the balloon, come into apposition with the walls of the target vessel and form blood flow paths around the protrusions.

BACKGROUND PRIOR ART

The technique of percutaneous transluminal coronary angioplasty (PCTA), wherein a preshaped or flexible guiding catheter is introduced into a cardiovascular system through the femoral or brachial artery under local anesthesia, is known in art. The guiding catheter is positioned in the entrance of the target coronary artery. A dilatation catheter with an expandable balloon tip is advanced through the guide catheter and manipulated into the branches of the coronary artery until the balloon is appropriately centered on the stenotic target lesion. The balloon is then inflated with a radiopaque contrast, which is a liquid that enables one to locate the position of the catheter using X-rays. The balloon applies pressure in a direction generally radial to the vessel wall to compress and remold the atherosclerotic material into a significantly more patent internal configuration. Current balloon dilatation catheters employ a fixed or movable steerable guide wire which negotiates the serpentine coronary vasculature in an atraumatic fashion to provide a path for the passage of the dilatation catheter.

Inflation of conventional dilatation balloons completely blocks the artery, and thus interrupts distal coronary blood flow. The duration of balloon inflation is of necessity limited by the resulting coronary ischemia, and manifest or incipient clinical instability. Typical inflation times may range from 15 seconds to 120 seconds. Maintenance of coronary perfusion during dilatation would greatly enhance the safety of coronary angioplasty, particularly in vessels serving large areas of myocardium. Prolonged inflation times would also be desirable to increase the likelihood of adequate vessel patency post-dilatation. Prolonged balloon inflation times also increase the probability of maintaining vessel patency or opening, following abrupt arterial closure due to intimal disruption, vessel dissection, or endoluminal thrombus formation.

In addition, it is known that the process of angioplasty injures the inner surfaces of the involved artery. It is believed that a condition known as restenosis is to some degree initiated by this injury to the artery. Restenosis is the recurrence of severe renarrowing in a coronary artery at the site of prior angioplasty, and to some degree, the condition of restenosis involves the growth and proliferation of scar tissue initiated by angioplasty. Thus, there is a need for balloon designs resulting in a lesser degree of vessel wall injury than that caused by current balloon designs. Current balloon designs have more surface area in contact with the vessel wall and are therefore more likely to cause extensive disruption to the cellular lining of the vessel.

Therefore, it would be desirable for an angioplasty catheter to provide for continuous blood flow (perfusion) past the stenotic region in the target coronary vessel even during periods of balloon inflation, and to provide for a lesser degree of vessel wall injury upon inflation. Such a perfusion dilatation catheter would permit prolonged balloon inflations to achieve the advantages elaborated above without provoking clinical instability, as long as the inflated balloon catheter assembly provides physiologically adequate coronary flow rates. However, in order for a perfusion angioplasty catheter to be of true clinical utility and suitable for routine use as the dilatation catheter of first choice by medical practitioners of the art, it must additionally incorporate advances available in the current genre of angioplasty catheters. Some of these advances include: balloons having a small diameter when collapsed, so as to enable the balloon to pass through abnormal areas of extreme constriction or blockage; balloons having excellent tracking ability over steerable coronary guide wires, such that the balloons conform to the paths of the guide wires; and balloons having enhanced pushability through tortuous coronary circulation and through severely stenotic lesions.

Numerous angioplasty catheters which afford varying degrees of coronary perfusion during balloon inflation have been described in the prior art. However, none of these catheters incorporate all of the necessary attributes mentioned above into a single device, and hence these catheters are not suitable for widespread first line use.

U.S. Pat. No. 4,790,315, to Mueller, Jr. et al. discloses a perfusion catheter wherein small holes are placed in the hollow shaft of the catheter adjacent to the proximal and distal ends of the balloon. These holes provide a flow path for blood during the angioplasty process and if the vessel collapses following dilatation. The cross-sectional area provided for flow, however, is small and suboptimal.

U.S. Pat. No. 4,877,031 to Conway et al. discloses a steerable perfusion dilatation catheter with a fixed guide wire assembly. The steerable guide wire in this device is integral to the dilatation catheter and does not have to be removed to optimize coronary flow during balloon inflation. This device, however, again provides limited cross-sectional area for coronary blood flow and exhibits an increased collapsed crossing profile which limits its ability to traverse lesions of critical stenotic severity. Any increase in the cross-sectional area of the hollow central balloon catheter shaft to augment perfusion rates further increases the crossing profile and also decreases its desirable flexibility and tracking properties.

U.S. Pat. No. 4,581,017 to Sahota also discloses a perfusion balloon wherein flow is achieved during balloon inflation through the hollow central shaft of the catheter by means of proximal and distal shaft side holes. In addition, Sahota discloses angioplasty catheters of complex construction which incorporate multiple small balloons deployed circumferentially around a central hollow shaft and which further incorporate multiple individual tubular ports for inflation and deflation of the balloon subunits. Some designs use a single dilating balloon in which significantly thickened portions of the balloon wall are provided for non-uniform compliance during inflation. The complex construction of the balloons of Sahota severely decreases their flexibility, trackability, and markedly increases their lesion crossing profile. These limitations have continued to prevent adaptation of balloons of said design to clinical art.

Similar limitations apply to the steerable perfusion angioplasty dilatation catheter disclosed in U.S. Pat. No. 4,892,519 to Songer et al. The device of Songer et al. also has an integral but movable guide wire which cannot be removed or replaced if the technical complexities of the procedure require it.

U.S Pat. No. 4,909,252 to Goldberger discloses a perfusion angioplasty balloon having a donut-shaped cross-section with a central opening which provides for blood flow through a passage, when the balloon is inflated. This device, however, utilizes a complex balloon geometry requiring redundant balloon surface folds which greatly enlarge the collapsed crossing profile of the angioplasty balloon and also limit the flexibility and tracking of the distal balloon assembly.

U.S. Pat. Nos. 4,601,713, 4,710,181, and 4,738,666, all to Fuqua, and European Patent No. 400,713 to Deuss, disclose balloon catheters wherein an expandable balloon tip capable of exhibiting several discrete diameters is achieved. The balloon material folds on itself redundantly in the longitudinal dimension to provide one or more invaginations which are constrained either by an external retaining sheath or by heat welds of limited strength. The balloon catheter achieves a second and larger diameter when the constraints are physically removed or are overcome by sufficient inflation pressure. The folds of these longitudinal invaginations, however, are in contiguity and do not afford blood flow during balloon inflation.

It is apparent that what has been needed and heretofore unavailable are perfusion angioplasty balloon catheters which provide excellent and physiologically adequate coronary blood flow past the area of lesion stenosis without compromising or limiting other necessary and desirable properties of the angioplasty catheter assembly. These attributes, as outlined above, include the low lesion crossing profile, fully exchangeable guide wire capability, and favorable tracking, flexibility, and longitudinal force transmission characteristics provided by the current genre of non-perfusion angioplasty balloon catheters. The present invention satisfies these needs.

SUMMARY OF THE INVENTION

The present invention relates to dilatation catheters. Specifically, the perfusion dilatation catheter of the present invention is used in coronary angioplasty, but it is equally applicable to angioplasty of blood vessels in other locations. The catheter is comprised of a flexible elongated tubular shaft having proximal and distal ends. An expandable inflatable balloon is affixed near the distal end of the shaft and surrounds the shaft. Upon expansion, the balloon becomes non-circular, and the balloon s cross-section is circumscribed by the circular perimeter of the target vessel cross-section. The balloon tip, upon expansion, has at least two rounded apices which come into apposition with the walls of the target vessel. The maximum height of the apices does not exceed the nominal radius of the target vessel, and multiple radii of the balloon tip cross-section are of lesser radial dimension than the nominal radius of the target vessel. Thus, due to the unique shape and configuration of the balloon, a path for blood to flow past the balloon tip, during expansion, is formed through the areas of submaximal tip radial dimension.

The remaining structural features of the dilatation catheter are conventional. For example, the long tubular shaft may have one or two lumens. If the catheter is of the type having one lumen, this lumen is in communication with the interior of the balloon and provides for the balloon's inflation, deflation, and venting of air. The dilatation catheter having one lumen is constructed upon a flexible, steerable fixed guide wire system. If the catheter is of the type having two lumens, the first lumen extends partially or entirely through the balloon shaft and is out of communication with the interior of the balloon. However, this lumen is of suitable construction to accept a flexible, steerable guide wire. The second lumen is in communication with the interior of the balloon and provides for its inflation, deflation, and venting of air.

It is the among the objects of the present invention to provide a new and improved perfusion dilatation catheter.

It is another object of the present invention to provide a perfusion dilatation catheter wherein the catheter allows continuous and substantial blood flow past the balloon at all times during inflation and which allows for prolonged inflation periods without compromising clinical stability.

It is another object of the present invention to provide a perfusion dilatation catheter having an inflatable balloon affixed near a distal end of a tubular shaft wherein the balloon surrounds the circumference of the shaft.

It is another object of the present invention to provide a perfusion dilatation catheter wherein blood flows past the inflated balloon during balloon inflation as a consequence of the novel cross-sectional geometry of the inflated balloon.

It is another object of the present invention to provide a perfusion dilatation catheter in which the angioplasty balloon has such a configuration so as to exert pressure during balloon inflation against the vessel wall at discrete, focal portions of vessel perimeter to transform the area of atherosclerotic narrowing from a stenotic to an unobstructed configuration.

It is another object of the present invention to provide a perfusion dilatation catheter in which the angioplasty balloon has a configuration which may result in a lesser degree of vessel wall injury than current balloons since the balloon of the present invention has less surface area in contact with the vessel wall and is therefore less likely to cause as much disruption to the cellular lining.

It is another object of the present invention to provide a perfusion dilatation catheter where the rate of blood flow distal to the site of balloon inflation is independent of, and not limited by, the diameter of the hollow central shaft of the dilatation catheter and the geometry of the shaft side holes which permit entrance and exit of blood through the central hollow shaft.

It is another object of the present invention to provide a perfusion dilatation catheter in which distal blood flow during balloon inflation does not require withdrawal of the guide wire from the coronary artery distal to the site of balloon inflation, notwithstanding the fact that the guide wire is fully removable and exchangeable.

It is another object of the present invention to provide a perfusion dilatation catheter in which the inflated balloon cross-sectional geometry provides for distal blood flow during balloon inflation such that perfusion during inflation is independent of the dilatation catheter shaft geometry and construction. The balloon tip can be manufactured on dilatation catheters which incorporate existing or new fabrications to enhance their steerability, pushability or tracking characteristics.

It is another object of the present invention to provide a perfusion dilatation catheter having minimal deflated balloon lesion crossing diameter, notwithstanding the ability of the perfusion dilatation catheter to sustain physiologically adequate coronary blood flow during balloon inflation.

It is another object of the present invention to provide a perfusion dilatation catheter in which the catheter can be left in situ to maintain coronary blood flow and stabilize the vessel in an open configuration for a protracted period of time. This serves as a removable temporary "stent" (a scaffold lying within the lumen used to provide support or to assure patency of an intact lumen) in the event the target vessel is dissected or disrupted, and thereby avoids the need for emergency coronary bypass surgery.

It is another object of the present invention to provide a perfusion dilatation catheter in which the catheter can be left in situ if clinically necessary to maintain coronary blood flow and stabilize the vessel in an open configuration for a protracted period of time. This serves as a removable temporary "stent" in the case of a "failed" angioplasty in which emergency coronary bypass surgery or other stabilizing or salvage procedures are required.

Additional objects and features of the invention will appear from the following description in which the preferred embodiments are set forth in detail in conjunction with the accompanying drawings.

DETAILED DESCRIPTION OF A PREFERRED EMBODIMENT

It will be apparent to one familiar with the art that various balloon configurations which achieve the benefit of the above designs can be constructed with balloons of specialized cross-sectional shape such that their cross-sections are circumscribed by the circular perimeter of the target vessel cross-sections. The balloon tip should possess at least two rounded apices, and the maximum height of the apices should not exceed the nominal radius of the target vessel. In addition, multiple radii of the balloon cross-section are of lesser radial dimension than the nominal radius of the target vessel, thus forming a path for blood to flow past the balloon during expansion through the areas of submaximal balloon radial dimension.

The foregoing objects are achieved in accordance with the present invention by providing a balloon dilatation catheter having one of several different configurations of its shaft and proximal sections, so as to exploit current technologies and provide the desired attributes of the flexible tubular member having one or two lumens extending therethrough. If the catheter is of the type having one lumen, this lumen is in communication with or integral with the interior of the balloon and provides for the balloon's inflation, deflation, and venting of air. The dilatation catheter having one lumen is constructed upon a flexible, steerable, fixed guide wire system. If the catheter is of the type having two lumens, the first lumen extends either partially or entirely through the balloon shaft and is out of communication with the interior of the balloon. However, this lumen is of suitable construction to accept a flexible, steerable guide wire. The second lumen is in communication with or integral with the interior of the balloon and provides for its inflation, deflation, and venting of air.

Figure 1:
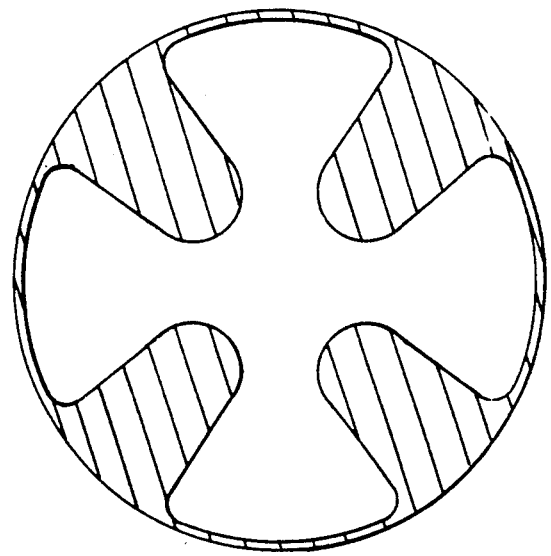
FIG. 1 is a cross-sectional view of a perfusion dilatation balloon configuration with four symmetrical areas of radial vessel wall contact. The lined areas remain partially or totally unobstructed during balloon inflation to permit maintenance of coronary perfusion.

FIG. 1 is a cross-sectional view of one embodiment of a perfusion dilatation balloon configuration of the present invention having four symmetrical areas of radial vessel wall contact. The lined areas remain partially or totally unobstructed during balloon inflation to permit maintenance of coronary perfusion. A first tubular element 1 having a first lumen 2 is shown at the center of the dilatation balloon.

Figure 2:
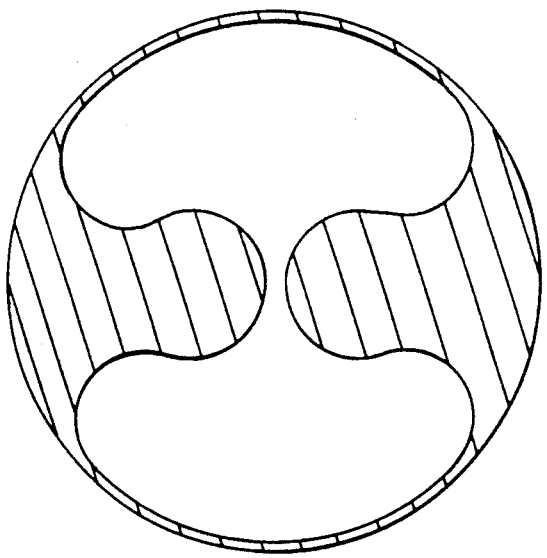
FIG. 2 is a cross-sectional view of a perfusion dilatation balloon configuration with rounded contact areas at both ends of its diameter, such that upon inflation, the dilatation balloon exerts radial force on the obstructing vessel lesion at two lateral areas. The lined areas remain available to permit ongoing perfusion.

FIG. 2 is a cross-sectional view of an embodiment of a perfusion dilatation balloon configuration of the present invention having rounded contact areas at both ends of its diameter, such that upon inflation, the dilatation balloon exerts radial force on the obstructing vessel lesion at two lateral areas. The lined areas remain available to permit ongoing perfusion.

Figure 3:
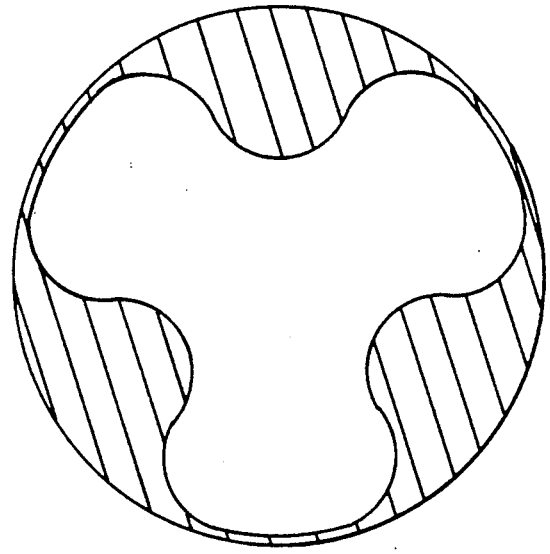
FIG. 3 is a cross-sectional view of a dilatation balloon which affords three areas of balloon to vessel wall contact during balloon inflation, while still leaving large unobstructed areas within the artery to permit continuous coronary flow. The lined areas represent areas of ongoing perfusion.

FIG. 3 is a cross-sectional view of an embodiment of a perfusion dilatation balloon which affords three areas of balloon to vessel wall contact during balloon inflation, while still leaving large unobstructed areas within the artery to permit continuous coronary flow. The lined areas represent areas of ongoing perfusion.

Figure 4:
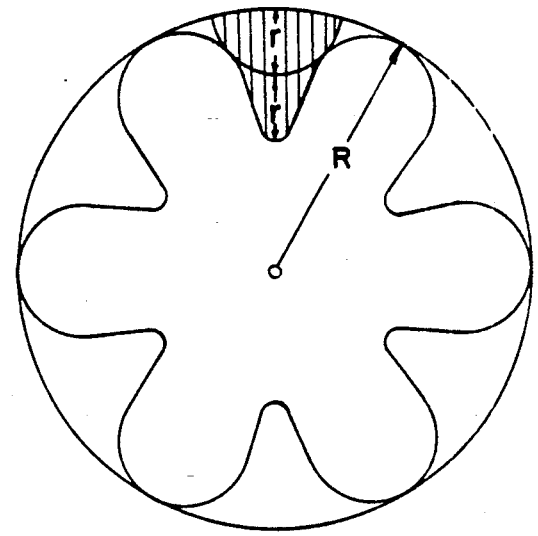
FIG. 4 is a cross-sectional view of a six pod balloon configuration which both increases the sites of inflated balloon-vessel contact and maintains large areas for perfusion (lined areas). If the radius (r) of the contact pods of the inflated balloon are ¼ that of the maximal inflated balloon diameter R), more than 20% of the intravascular arterial area remains potentially available during balloon inflation to sustain coronary perfusion.

FIG. 4 is a cross-sectional view of an embodiment of a perfusion dilatation balloon having a six pod balloon configuration which both increases the sites of inflated balloon-vessel contact and maintains large areas for perfusion (lined areas). If the radius (r) of the contact pods of the inflated balloon are ¼ of the length of the maximal inflated balloon diameter (R), then more than 20% of the intravascular arterial area remains potentially available during balloon inflation to sustain coronary perfusion.

By way of example, the dilatation catheter of the present invention in one embodiment (FIG. 5) consists of a first tubular element 1 having a first lumen 2 extending the length of the first tubular element 1. A second tubular element 3 is coaxially disposed on the first tubular element 1 and has a second lumen 5 which extends longitudinally along the length of the first and second tubular elements. An expandable balloon 4 is carried by the second tubular element 3 near the distal portion thereof, and has its interior in communication with the second lumen 5. The balloon 4 extends concentrically around and surrounds the circumference of the first tubular element 1. The balloon can be formed as a separate element which has its extremities bonded to the second tubular element 3, or it can be formed integral with the second tubular element 3. The tubular elements 1 and 3 are formed of a suitable thermo-plastic polymer, such as, but not necessarily limited to, polyolefin or polyvinylchloride, both of considerable flexibility and strength. A radiopaque marker 6 is affixed to the first tubular element 1 which acts to locate and track the balloon under X-ray.

The construction of the expandable balloon catheter tip having a complex non-circular cross-sectional configuration is achieved by one of several different methods, and any of the following methods may be used, alone or in combination, regardless of whether the balloon is formed as a separate element or is integral with the second tubular element.

One method of manufacturing the balloon includes using heat and a mold, i.e., a glass mold, and shaping the balloon so as to impart the desired configuration to the balloon. The mold is coated with silicone or another lubricant to prevent adherence of the balloon to the mold. Then a thermoplastic polymer is heated and shaped by expanding it under pressure to conform to the mold so as to form the desired configuration of the balloon.

A second method of manufacturing the balloon and forming it into a desired geometric shape includes heat sealing or otherwise securely bonding thin strips of an inelastic polymer or other noncompliant material longitudinally along the central axis of the balloon, so as to constrain the expansion of portions of the balloon perimeter during inflation. By constraining portions of the balloon perimeter during its expansion, one can achieve the desired configuration of the balloon.

Finally, a balloon can be shaped to the desired configuration by applying heat to specifically designated areas of the balloon material so as to cause shrinkage only to those areas of the balloon. The balloon is then shaped into the desired geometric configuration. Several of the above-mentioned techniques may be used in any sequence to construct a single balloon tip of complex geometry.

Figure 5:
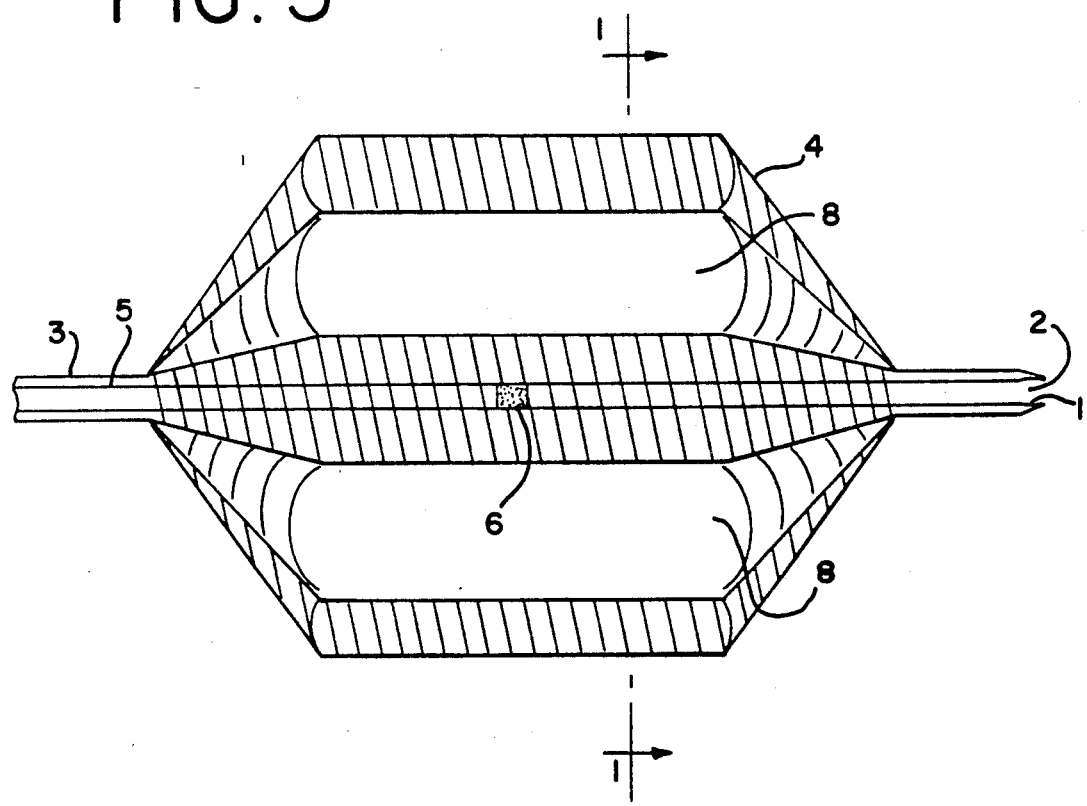
FIG. 5 is a perspective view of the balloon portion of a dilatation catheter having an expandable balloon tip of the cross-sectional configuration shown in FIG. 1.

The balloon is preferably formed of a suitable thermoplastic polymer which provides for thin walls having great strength. A variety of thermoplastic polymers which can be formed in a mold or blown when appropriately heated can be used. The balloon in its preferred embodiment (FIG. 5) can have an outside diameter ranging from about 2.0 to 4.0 millimeters with a wall thickness as thin as 0.025 millimeters. The balloon will generally be from about approximately 2 cm to 6 cm in length. Such a balloon can be inflated to pressures in the range of up to 10 to 15 atmospheres. A radiopaque marker 6 is affixed to the first tubular element 1 to locate and track the balloon under X-ray. A venting lumen may be provided in the distal end of the balloon to facilitate its preparation, or the balloon can be filled directly with radiopaque contrast following aspiration. The remaining structural features of the balloon dilatation catheter shown in FIG. 5 are conventional.

For example, a conventional side arm adapter having a central arm and a side arm can be used, and it is connected to the lumen of the catheter. A guide wire extends through the central arm through the first lumen 2 of the first tubular element 1. The distal element of the guide wire extends past the distal element of the dilatation catheter. A torquer is secured to the proximal portion of the guide wire and allows extension, retraction, and rotation of the guide wire.

Use of the perfusion balloon dilatation catheter is now briefly described. The dilatation catheter (shown in its inflated configuration in FIG. 5) is purged of air, filled with suitable radiopaque contrast, deflated and inserted into a guiding catheter (not shown) already positioned in a conventional manner in the target vessel of the patient. The dilatation catheter is prepared prior to use in the conventional manner by expelling air from within the balloon lumen by displacing it with suitable contrast injected with a standard inflation device. The balloon catheter is advanced with the aid of a steerable guide wire system. The balloon is centered on the lesion with the help of the mid-point radiopaque marker. When inflated, the balloon exerts force radially against the obstructing plaque. Coronary autoperfusion is maintained during the period of inflation through areas 8 as the result of the unique cross-sectional geometry of the balloon. The perfusion catheter of this design is particularly suited for treating lesions which have dissected and have a flap and which are difficult to keep open after a standard balloon has been removed. The perfusion catheter permits the flap to be held against the vessel wall for a substantially longer period of time than with a standard balloon catheter, for example, 2-15 minutes or even hours, rather than the conventional inflation time of 30-120 seconds. The prolonged treatment greatly increases the likelihood that the vessel will remain patent once the balloon is removed. The perfusion catheter of this design is well suited as the catheter of first choice for most routine angioplasties, and it has specific advantages for approaching lesions in vessels which serve large and critical areas of myocardium.

As indicated above, the present invention has a number of important advantages and features. Because the dilatation catheter permits blood flow past an inflated balloon, it permits the balloon to remain inflated substantially longer than is possible with non-perfusion balloons heretofore provided. A dilatation angioplasty catheter with a balloon tip having the configurations illustrated in the Figures allows blood to continue to flow past the expanded balloon during balloon inflation, and affords prolonged inflation duration without engendering significant myocardial or end organ ischemia. The high flow rates achievable during periods of balloon inflation are the result of the geometry of the inflated balloon and are not dependent on the diameter of the hollow balloon shaft. This allows construction of balloon tip catheters of low lesion crossing profile which can incorporate various advances in shaft composition and construction technology to maximize desirable tracking and longitudinal force transmission properties. Furthermore, because distal coronary perfusion during balloon inflation is not achieved through the hollow balloon shaft, the most distal tip of the balloon shaft does not have to protrude one or more centimeters distal to the balloon itself or be of a relatively large caliber. This configuration avoids the technical difficulty encountered from time to time in appropriately positioning perfusion balloons of conventional design, and avoids the danger of distal vessel trauma associated with the use of perfusion catheters of conventional design. Also, because the various designs of the balloon of the present invention have, upon inflation, less surface area in contact with the vessel wall, the balloons of the present invention are probably less likely to cause as much disruption to the cellular lining of the vessel as current balloons, and they may reduce the frequency and severity of lesion restenosis. The balloons of the present invention are simple to construct, and the efficiency of their design and manufacture avoids significant increases in their deflated bulk, stiffness, and lesion crossing profiles.

It is apparent that a new and improved dilatation catheter and method of manufacturing of the same have been provided. While only certain presently preferred embodiments have been described in detail, it will be apparent to those familiar with the art that certain changes and modifications can be made without departing from the scope of the invention as defined by the following claims. This disclosure describes multiple transluminal angioplasty balloon configurations with clinical efficacy, with the invention limited only by the requirement that each balloon design provide sufficient expansion of the artery to reduce the area of stenosis to a clinically acceptable residual, and simultaneously provide adequate intravascular flow during prolonged balloon inflation to avoid clinically detrimental ischemia. These designs are equally applicable to conventional central lumen over-the-wire, fixed steerable wire, and rapid exchange "mono-rail" shaft technologies. Various angioplasty balloon configurations which achieve this result are disclosed in the present invention, but the invention is not limited solely to the configurations illustrated. It will be obvious to one skilled in the art that various configurations can be used in accordance with the principles herein disclosed.

What I claim is:

1. A dilatation catheter adapted for insertion into a target vessel and subsequent inflation therein, the catheter comprising:
   a flexible elongated tubular shaft having proximal and distal ends defining at least one lumen and adapted for receiving a guide wire; and,
   an inflatable balloon affixed near said distal end of said shaft and surrounding the circumference of said shaft, said balloon having a wall of substantially constant thickness and at least two substantially rounded axial protrusions formed in said wall said protrusions having a common internal chamber with substantially no internal boundaries, wherein upon expansion of said balloon, said protrusions come into apposition with the walls of said target vessel, such that said balloon upon expansion, becomes non-circular, thereby forming blood flow paths around said protrusions.

2. The catheter of claim 1 wherein said target vessel has a nominal radius, and wherein said protrusions of said balloon, upon expansion, have a maximum height which does not exceed said nominal radius of said target vessel, and further wherein multiple radii of said balloon's cross-section, said multiple radii extending from a center of said tubular shaft to an outer surface point of said balloon, are of lesser radial dimension than said nominal radius of said target vessel.

3. The catheter of claim 1 including a radiopaque marker affixed to said shaft.

4. The catheter of claim 1 wherein said lumen of said tubular shaft is in communication with or is integral with an interior of said balloon, said lumen providing for the inflation of said balloon.

5. The catheter of claim 1 wherein said tubular shaft has a first lumen extending longitudinally through said shaft and being out of communication with the interior of said balloon, and a second lumen in communication with or integral with said interior of said balloon, said second lumen providing for the inflation and deflation of said balloon.

6. The catheter of claim 5 wherein said first and second lumen are a thermo-plastic polymer.

7. The catheter of claim 5 wherein said second lumen provides a surface on which to carry said balloon.

8. A dilatation catheter adapted for insertion into a target vessel and subsequent inflation therein, the catheter comprising:
   a flexible elongated tubular shaft having proximal and distal ends defining at least one lumen and adapted for receiving a guide wire;
   an expandable, inflatable tip affixed near said distal end of said shaft and surrounding the circumference of said shaft, wherein upon expansion of said tip concentrically around said shaft, said tip has a cross-section circumscribed by a circular perimeter of a cross-section of said target vessel;
   said target vessel having a nominal radius and said tip having a wall of substantially constant thickness and at least two rounded apices formed in said wall, said apices having a common internal chamber substantially with no internal boundaries, wherein a maximum height of said apices does not exceed said nominal radius of said target vessel, and further wherein multiple radii of said tip cross-section, said multiple radii extending from a center of said tubular shaft to an outer surface point of said tip, are of lesser radial dimension than said nominal radius of said target vessel;
   wherein said tip, upon expansion, forms a path for blood to flow past said tip and through areas of submaximal tip radial dimension.

9. The catheter of claim 8 wherein said expandable tip is a balloon.

10. The catheter of claim 8 including a radiopaque marker affixed to said shaft.

11. The catheter of claim 8 wherein said lumen of said tubular shaft is in communication with or is integral with an interior of said tip, said lumen providing for the inflation of said tip.

12. The catheter of claim 8 wherein said tubular shaft has a first lumen extending longitudinally through said shaft and being out of communication with the interior of said tip, and a second lumen in communication with or integral with said interior of said tip, said second lumen providing for the inflation and deflation of said tip.

13. The catheter of claim 12 wherein said first and second lumen are a thermo-plastic polymer.

14. The catheter of claim 12 wherein said second lumen provides a surface on which to carry said tip.

15. A dilatation catheter adapted for insertion into a target vessel and subsequent inflation therein, the catheter comprising:

a flexible elongated tubular shaft having proximal and distal ends defining at least one lumen and adapted for receiving a guide wire;

an inflatable balloon tip affixed near said distal end of said shaft and surrounding the circumference of said shaft, said balloon tip having a wall of substantially constant thickness and at least two substantially rounded axial protrusions formed in said wall, said protrusions having a common internal chamber with substantially no internal boundaries, and wherein upon expansion of said balloon tip concentrically around said shaft, said balloon tip has a cross-section having at least two arcs of contact with said target vessel perimeter;

said target vessel having a nominal radius and said arcs having a radius which is substantially equal in length to said nominal radius of said target vessel, and further wherein said arcs have multiple areas of lesser radial dimension than said nominal radius of said target vessel;

said balloon tip, upon expansion, forming a path for blood to flow past said balloon tip and through areas of submaximal tip radial dimension.

16. The catheter of claim 15 including a radiopaque marker affixed to said shaft.

17. The catheter of claim 15 wherein said lumen of said tubular shaft is in communication with or is integral with an interior of said balloon, said lumen providing for the inflation of said balloon.

18. The catheter of claim 15 wherein said tubular shaft has a first lumen extending longitudinally through said shaft and being out of communication with the interior of said balloon, and a second lumen in communication with or integral with said interior of said balloon tip, said second lumen providing for the inflation and deflation of said balloon tip.

19. The catheter of claim 18 wherein said first and second lumen are a thermo-plastic polymer.

20. The catheter of claim 18 wherein said second lumen provides a surface on which to carry said balloon.

* * * * *